United States Patent
Markowitz et al.

(10) Patent No.: US 6,416,745 B1
(45) Date of Patent: Jul. 9, 2002

(54) DENTAL COMPOSITION FOR TREATING HYPERSENSITIVE TEETH

(75) Inventors: Kenneth J. Markowitz, Fanwood, NJ (US); Benjamin D. Fitz, Brooklyn, NY (US)

(73) Assignee: Block Drug Company, Inc., Jersey City, NJ (US)

( * ) Notice: Subject to any disclaimer, the term of this patent is extended or adjusted under 35 U.S.C. 154(b) by 0 days.

(21) Appl. No.: 09/848,138

(22) Filed: May 3, 2001

(51) Int. Cl.$^7$ .......................... A61K 7/16; A61K 9/127
(52) U.S. Cl. .......................... 424/49; 424/450
(58) Field of Search .................. 424/49–55, 450

(56) References Cited

U.S. PATENT DOCUMENTS

| | | | |
|---|---|---|---|
| 3,863,006 A | | 1/1975 | Hodosh .................. 424/49 |
| 4,634,589 A | | 1/1987 | Scheller ................. 424/49 |
| 4,767,615 A | | 8/1988 | Geho et al. ............. 424/57 |
| 5,104,661 A | * | 4/1992 | Lau ...................... 424/49 |
| 5,211,939 A | | 5/1993 | Turesky et al. ......... 424/49 |
| 5,270,031 A | | 12/1993 | Lim et al. .............. 424/49 |
| 5,589,159 A | | 12/1996 | Markowitz et al. ..... 424/49 |
| 5,717,030 A | * | 2/1998 | Dunn et al. ............ 523/111 |
| 5,735,942 A | | 4/1998 | Litkowski et al. ..... 106/35 |
| 5,853,755 A | * | 12/1998 | Foldvari ................ 424/450 |
| 5,891,233 A | | 4/1999 | Salonen et al. ........ 106/35 |
| 5,922,332 A | * | 7/1999 | Fossel .................. 424/450 |
| 5,935,599 A | * | 8/1999 | Dadey ................... 424/450 |
| 6,045,823 A | * | 4/2000 | Vollhardt et al. ...... 424/450 |
| 6,153,219 A | * | 11/2000 | Creeth et al. .......... 424/451 |
| 6,228,347 B1 | * | 5/2001 | Hersh ................... 424/49 |
| 6,261,597 B1 | * | 7/2001 | Kurtz ................... 424/450 |

FOREIGN PATENT DOCUMENTS

| | | | |
|---|---|---|---|
| CA | 2053346 | * | 4/1992 |
| DE | 19922193 | * | 11/2000 |
| EP | 481701 | * | 4/1992 |
| EP | 613685 | * | 9/1994 |
| WO | 9001923 | * | 3/1990 |
| WO | 92 20319 | * | 11/1992 |

OTHER PUBLICATIONS

Fujisawa et al (I) J. Dent. Res. 61(10): 1206–1210, 1982.*
Fujisawa et al (II) J. Biomed. Mater. Res. 21(1):89–98, 1987.*

* cited by examiner

*Primary Examiner*—Shep K. Rose
(74) *Attorney, Agent, or Firm*—Nora Stein-Fernandez

(57) ABSTRACT

The present invention provides dental compositions and methods for treating dentinal hypersensitivity teeth based on the discovery that anionic liposomes possess the capacity to induce mineral formation in the dentinal tubules which partially or fully block them. The subject compositions comprise the liposomes and a suitable carrier and are advantageous in that they can deliver additional agents useful in the treatment of dentinal hypersensitivity, particularly nerve desensitizing agents, to the tubules. The liposomes of the invention are further advantageous in that they are stable to conventional sources of fluoride ion conventionally used as anti-caries agents. The methods of the present invention utilize the subject composition to effect blocking of the dentinal tubules and to simultaneously deliver other treatment agents such as nerve desensitizing agents for the combined benefits thereof.

27 Claims, No Drawings

DENTAL COMPOSITION FOR TREATING HYPERSENSITIVE TEETH

The present invention relates to compositions and methods for the treatment of dental hypersensitivity.

BACKGROUND OF THE INVENTION

Dentinal hypersensitivity is a temporary induced pain sensation produced when hypersensitive teeth are subjected to changes in temperature and/or pressure or to chemical action. Hypersensitivity may occur whenever the dentin of a tooth is exposed by attrition or abrasion, or when the tooth's finer root surface is exposed by periodontal disease. Dentin is a bone-like material in teeth that is usually covered by enamel above the gum line and cementum below the gum line. The enamel or cementum may be removed through decay, injury, disease or other causes, thereby exposing the dentin to external stimuli in the mouth. Dentin generally contains channels, called tubules, that allow material and energy transport between the exterior of the dentin and the interior of the tooth where the nerve is located. One theory of dentinal hypersensitivity, called the hydrodynamic theory, suggests that exposure of these tubules to external stimuli can cause irritation of the nerve and lead to the discomfort of hypersensitivity. The hydrodynamic theory suggests that hypersensitivity may be treated by making the nerve in the tooth less sensitive to stimuli, or by blocking or occluding the tubules to prevent or limit exposure of the nerve to external stimuli.

Many attempts have been made to control dentinal hypersensitivity. One approach is to reduce the excitability of the nerve in a sensitive tooth. This technique interferes with the ordinary triggering process of the nerve by altering the chemical environment of the nerve through the use of agents to make the nerve less sensitive. These agents are generally referred to as "nerve agents" or "nerve desensitizing agents". The most well-known agent for this purpose is potassium nitrate, used in commercial dentifrices for sensitive teeth and discussed in U.S. Pat. No. 3,863,006. Examples of other agents known as nerve desensitizing agents are potassium salts such as potassium bicarbonate and potassium chloride and the like. Another approach to controlling dentinal hypersensitivity, as discussed above with regard to the hydrodynamic theory, is the use of agents to fully or partially occlude tubules. Examples of such "tubule blocking agents" include the following: charged polystyrene beads, U.S. Pat. No. 5,211,939; apatite, U.S. Pat. No. 4,634,589; a polyacrylic acid polymer having a typical molecular weight from about 450,000 to about 4,000,000, U.S. Pat. No. 5,270,031; and certain clays, U.S. Pat. No. 5,589,159. Still others have attempted to treat dentin sensitivity by inducing the growth of mineral inside the dentinal tubules. A further approach described in U.S. Pat. No. 5,735,942 to Litkowski and U.S. Pat. No. 5,891,233 to Salonen et al. is the use of bioactive glass to treat tooth sensitivity. In general, these inventions suffer from problems of fluoride compatibility and these inorganic solids are abrasive materials.

It is apparent that a considerable amount of work has been done with regard to the problem of dentinal hypersensitivity. Despite these efforts, however, there is still a need for an effective, improved dentinal formulation for treating dentinal hypersensitivity. In accordance with the present invention, it has been discovered that compositions containing certain liposomes are effective in treating hypersensitivity. The compositions of the present invention are unique in that they are capable of inducing mineral formulation in dentinal tubules thereby occluding the tubules. The subject compositions are further unique in that, in addition to providing tubule blocking, the liposomes themselves have the capability to deliver nerve desensitizing agents, thereby also acting to reduce the excitability of the nerve to external stimuli.

SUMMARY OF THE INVENTION

The present invention relates to an orally acceptable formulation for the treatment of dentinal hypersensitivity containing liposomes capable of inducing mineral formation in the dentinal tubules and which may carry a further therapeutic agent, such as a desensitizing agent, for reducing the sensitivity of the nerve to external stimuli. The present invention also encompasses methods for the treatment of dentinal hypersensitivity utilizing compositions containing certain liposomes.

DETAILED DESCRIPTION OF THE INVENTION

The present invention provides a composition for treating hypersensitive teeth comprising a carrier suitable for oral health use and an effective amount of certain liposomes that have the capacity to induce mineral formation in the dentinal tubules thereby achieving tubule occlusion. Liposomes are well known materials as is their preparation from a wide variety of amphiphilic molecules. While liposomes have been utilized for a variety of applications in the health field, primarily as vehicles for various active substances, they have not been extensively used for dental preparations.

In those instances where liposomes have been proposed for used in dental preparations, it has been necessary to utilize a "target molecule" in order for them to adhere to dental hard tissue, such as enamel and dentin. The target functions like a tentacle that functions to anchor the liposome to dentin and enamel. For example, in U.S. Pat. No. 4,767,615, liposomes must be connected via chromium metal ions to another target molecule that has an affinity for hydroxyapatite.

Not all liposomes are effective at inducing mineral formulation. Therefore, the surface of the liposome is critical and it has been found in accordance with the present invention that the surface of the liposomes must be anionic. The anionic surface of these materials induces mineral formation by acting as a mineral template that attracts soluble mineral ions that are naturally present in the dentin tubular fluid and saliva. These liposome-surface-attracted soluble mineral ions precipitate from the dentin tubule fluid onto the liposome surface, which in turn, acts to nucleate mineral growth in the fluid. The mineral formed in the dentinal tubules will provide a massive insoluble plug, thereby restoring the tubules to their healthy, naturally impermeable state, blocking tubule fluid movement and insulating the dentinal nerves. The plugging action acts to impede subsequent transmission of material energy and pressure gradients through the dentin, and may also retard the penetration of oral bacteria or the by-products of bacterial metabolism, an added benefit.

Several investigations have shown that liposomes surfaces with phosphate groups neutralized with a monovalent metal ion, such as sodium or potassium, preferably the latter, have the requisite anionic surface and are effective in the present invention, while liposomes with a choline surface or inositol surface are not mineral-inducing. Preferably, the liposomes of the present composition are prepared from salts of diolylphosphatidic acid (DOPA, Avanti® Polar Lipids, Inc.). In order to penetrate and be retained in the dentinal tubules, the liposome diameter should not be greater than about 2 microns, preferably from about 0.1 to 1.5 microns, most preferably about 0.5 micron. Therefore, in a preferred embodiment, the present invention provides a dentifrice composition for treating hypersensitive teeth comprising an effective amount of a mineral-inducing liposome wherein the liposome is a potassium salt of DOPA, having a diameter not greater than 0.5 microns.

In addition to their capacity to function as tubule blocking agents as described above, the liposomes of the present invention provide a means of delivering additional agents, specifically nerve desensitizing agents into the dentinal tubules and releasing them therein in a controlled fashion. This is a significant advantage in that the overall effect of the subject preparations is enhanced by the action of two agents that function to treat dentinal hypersensitivity by two recognized mechanisms. Such nerve desensitizing agents include, for example, potassium salts such as nitrate, bicarbonate, chloride, citrate, and oxalate and other intradental nerve agents, such as capsaicin and eugenol, and certain other desensitizing salts such as strontium salts, for example the chloride, calcium chloride and the like.

The use of liposomes in accordance with the present invention possesses significant advantages over art-recognized inorganic treatments for biomineralization, such as disclosed in U.S. Pat. Nos. 5,735,942 and 5,891,233. The subject compositions are compatible with fluoride, can be prepared in an economically advantageous single-phase dentifrice tube and have no abrasivity.

The oral compositions of the present invention are typically formulated in the form of tooth pastes or gel dentifrices to be brushed on the teeth, or in the form of mouthwashes. However, other delivery systems may also be used. As non-limiting examples, the subject desensitizing agent can be formulated into a tooth powder, dentifrice, mouthwash, lozenge, buccal adhesive patch, oral spray, coatings that adhere to the oral cavity, chewing gum and the like. As these delivery forms are prophetic, higher or lower amounts of these agents may be combined to achieve the desired effect.

The subject dentifrice compositions contain the liposomes as described herein in between about 0.1 and 20% by weight, preferably between about 3 and 10% by weight. Particularly preferred in accordance with the present invention are dentifrice compositions in the form of a paste or gel that comprises 5% by weight of DOPA liposomes. The liposome may also be incorporated into other liposome membrane-compatible materials which can be used to tailor the release characteristics of any materials that the liposomes may carry. The liposomes may also be used to control the rate of in-tubule liposome biodegradation and to control other aspects of liposome stability.

The subject formulations may contain additional ingredients typically incorporated into oral health care compositions. Suitable ingredients include, without intended limitation, abrasive polishing materials, sudsing agents, flavoring agents, humectants, binders, sweetening agents, and water. Abrasives which may be used in the compositions of the invention include alumina and hydrates thereof, such as alpha alumina trihydrate, magnesium trisilicate, magnesium carbonate, aluminosilicate, such as calcined aluminum silicate and aluminum silicate, calcium carbonate, zirconium silicate, polymethylmethacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form that the oral composition is to take, the abrasive may be present in an amount up to 70% by weight, preferably 1 to 70% by weight, more preferably from 10 to 70% by weight, particularly when the composition is formulated into a toothpaste.

Humectants contemplated for use in the subject compositions include polyols, such as glycerol, sorbitol, polyethylene glycols, propylene glycol, hydrogenated partially hydrolyzed polysaccharides and the like. The humectants are generally present in amounts up to 80%, preferably 5 to 70%, by weight for toothpaste formulations. Thickeners suitable for use in the invention, typically silica, may be present at a level from about 0.1 to 20% by weight.

Binders suitable for use in the compositions of the invention include hydroxyethyl cellulose, and hydroxypropyl cellulose, as well as xanthan gums, Iris moss and gum tragacanth. Binders may be present in the amount from 0.01 to 10%. Sweeteners suitable for use, e.g. saccharin, may be present at levels of about 0.1% to 5%.

Fluoride sources as discussed above for delivering anticaries benefit, include those commonly used in oral health care compositions, such as sodium fluoride, stannous fluoride, sodium monofluorophosphate, zinc ammonium fluoride, tin ammonium fluoride, calcium fluoride and cobalt ammonium fluoride and the like. Preferred compositions in accordance with the present invention will include a fluoride source. Fluoride ions are typically provided at a level up to 1500 ppm, preferably 50 to 1500 ppm, although higher levels up to about 3000 ppm may be used as well.

Surfactants, such as a soap, anionic, nonionic, cationic, amphoteric and/or zwitterionic, may be present in amounts up to 15%, preferably 0.1 to 15%, more preferably 0.25 to 10% by weight. Anionic and/or nonionic surfactants are most preferred, such as sodium lauryl sulfate, sodium lauroyl sarcosinate and sodium dodecylbenzene sulfonate. Suitable flavors are usually included in low amounts, such as from 0.01 to about 5% by weight, especially from 0.1% to 5%.

Compositions in accordance with the present invention may, and preferably will, include antibacterial agents include, for example, phenolics and salicylamides, and sources of certain metal ions such as zinc, copper, silver and stannous ions, e.g. zinc, copper and stannous chloride, and silver nitrate. Such agents, in addition to other functional agents, including therapeutic agents and nutrients, may be incorporated into the liposomes themselves in accordance with the present invention.

Dyes/colorants suitable for oral health care compositions, i.e. FD & C Blue #1, FD & C Yellow #10, FD & C Red #40, etc., may be employed included in the subject formulations as well. Various other optional ingredients may also be included in the compositions of the invention such as preservatives, vitamins such as vitamins C and E, other anti-plaque agents such as stannous salts, copper salts, strontium salts and magnesium salts. Also included may be pH adjusting agents; anti-caries agents such as calcium glycerophosphate, sodium trimetaphosphate; anti-staining compounds such as silicone polymers, plant extracts and mixtures thereof. Additionally, polymers, particularly anionic polymers, such as polycarboxylates or polysulfonates, or polymers containing both a carboxylate and a sulfonate moiety, phosphonate polymers or polyphosphates may be included.

The various substances mentioned above are conventional ingredients suitable for oral care compositions, e.g., toothpastes, gels, mouthwashes, gums, powders, etc. Except where otherwise noted, references to toothpastes are to be construed as applying to gels as well. Mouthwash forms, e.g. mouthwashes, oral rinses and similar preparations, may be formulated as well. Such preparations typically comprise a water/alcohol solution, including a flavor component, humectant, sweetener, sudsing agent, and colorant. Mouthwashes can include ethanol at a level of from 0 to 60%, preferably from 5 to 30% by weight.

The present invention provides a method for treating dentinal hypersensitivity comprising treating the teeth with a therapeutically effective amount of the compositions as described herein. The method may consist of blocking, occluding, or sealing dentinal tubules with anionic liposomes having a diameter not greater than about two microns. Additionally, the method of the invention comprises providing via the liposomes of the subject compositions one or more additional therapeutic agents, preferably nerve desensitizing agents providing treatment for hypersensitivity via desensitization of the nerve as well. In other embodiments, at least one of the formulations and the liposomes may contain other functional agents, for example, nutritional, anti-caries, anti-bacterial and the like.

It is known in the art that liposomes may be formulated to withstand dissolution for a long period of time and may also be formulated, regardless of dissolution, to release a substance contained therein over a predetermined period of time. Both of these art-recognized techniques are incorporated within the scope of the present invention. Liposomes that resist dissolution over a considerable period of time are beneficial in providing sustained blockage of the tubules. By the same token, liposomes that would provide release of other therapeutic agents, particularly nerve desensitizers, over a period of at least several hours are beneficial in the combined therapeutic approach discussed above. Techniques for preparing liposomes that possess these characteristics of dissolution and release are known in the art and need not be detailed herein. Those of ordinary skill in the art will appreciate, however, that a dissolution and/or release profile will have to be established using conventional techniques for each given set of liposomes and one or more therapeutic agents.

A dentifrice composition in accordance with the present invention may be made by mixing the ingredients in any conventional manner, for example by creating a gel with the water and gelling agent and then adding the water soluble ingredients. Finally, a surfactant is added and the hydrophobic ingredients, including the liposomes, are then added with blending. The mixture is then packaged in a convention dentifrice container such as a tube, and applied to the surface of the teeth through conventional brushing, coating, painting or other direct or indirect application technique.

The instant invention will be further described with reference to the following non-limiting examples.

EXAMPLE 1

Hydraulic Conductance Evaluation

In order to test the desensitizing properties of liposomes as desensitizing agents, several oral compositions containing these materials were tested using the method described in U.S. Pat. No. 5,589,159. In this method, intact human molars free from caries and restorations are sectioned perpendicularly to the long axis of the tooth with a metallurgical saw to form thin sections, or discs, from about 0.4 to about 0.6 mm thick. Sections containing dentin and free of enamel are selected for testing and are then etched with an ethylenediaminetetraacetic acid solution to remove the smear layer. Each disc is mounted into a split chambered device described in J. Dent. Research, 57:187 (1978) which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs are wetted with human saliva to approximate intra-oral conditions. The apparatus includes a gas capillary tube mounted on a ruler or other measuring instrument. An air bubble is injected into the glass capillary tube. By measuring the displacement of the bubble as a function of time, fluid flow through the dentin disc can be measured.

Following measurement of the baseline fluid flow in the dentin disc, an experimental dentifrice is applied to the external surface with a nylon brush. After a defined period of brushing, the experimental material is rinsed off, and the post-application hydraulic conductance is measured. In this fashion, the ability of various experimental materials both alone and as components of dentifrice systems can be tested for the ability to obstruct fluid flow in the dentinal tubules. The percent flow reduction induced by brushing with the experimental materials can be calculated.

The reduction in flow immediately following liposome treatment show that the liposomes penetrate the tubules and adhere to the tubule walls, and are not washed out during the flow measurement. The flow measurements uses a pressure of 1 psi to induce flow through the dentin disks, a factor of 4.55 greater than the physiologically relevant pressure of 0.22 psi. The reduction in flow in a chronic model where the experimental material is applied twice daily to the external surface of the disk which is incubated in contact with sterile human saliva at 37° C. suggests that the liposomes have induced mineral-formation in the tubules which is confirmed by calcium depletion experiments as will be shown in Example 2. The flow reduction demonstrated by the application of 0.15% DOPA liposomes to the discs in the test described above was 28%. In the chronic model where exposure was continued for 40 hours as described above, the reduction was 62%.

EXAMPLE 2

Calcium Depletion Evaluation

Another method of evaluating the liposome's mineral-inducing capability of the liposome compositions of the present invention is to monitor the calcium depletion from a stimulated extra-cellular fluid (SBF, a solution having an ionic composition that is physiologically representative of blood plasma), upon introduction of liposomes. The SBF solution is metastable with respect to several solid mineral phases at room temperature. During the course of the experiment, the SBF sample containing added liposomes develops a precipitate, while the control sample without liposomes is entirely transparent. One of two 40 mL samples of SBF received 0.5 mL of a 0.15% solution of anionic liposomes. At 48 hours post treatment, the sample receiving the liposomes had developed a precipitate which was separated from the supernatant. The untreated SBF solution and the supernatant were analyzed for calcium. The initial SBF solution and the supernatant contained 65 ppm and 44 ppm calcium, respectively. Given the $0.50 \times 10^{-8}$ moles of DOPA present in the solution, if a [2 DOPA: 1 calcium] complex had occurred, the free calcium of the SBF would be depleted by approximately $2.5 \times 10^{31\ 3}$ ppm. The actual depletion of calcium was 21 ppm. This level demonstrates that significant mineralization had taken place since the depreciation is significantly higher than would be expected from only surfaces association.

These experiments demonstrate that mineral was induced from a meta-stable SBF solution and the precipitate formed was much greater than would be formed from calcium alone. Therefore, it is shown that the liposomes induced significant mineral formulation and the reduction in flow through dentin disks treated with 0.15% liposomes under the 40 hour chronic model are likely due to mineral formation in the dentinal tubules. In the chronic model, experimental formulations are applied to the discs every twice daily and the external surface of the discs is exposed to sterile human saliva at 37° C. between treatments.

EXAMPLE 3

Desensitizing Dentrifice (Prophetic) A desensitizing dentifrice in accordance with the invention may be made by combining the ingredients given below in accordance with accepted formulation techniques:

| Ingredient | Percent by Weight |
| --- | --- |
| Water | 30.0 |
| Potassium Nitrate | 5.0 |
| Hydrated Silica | 12.0 |
| Fumed Silica | 1.0 |
| Sodium Fluoride | 0.2 |
| Sorbitol Solution (70%) | 25.8 |
| Carboxymethyl Cellulose | 2.0 |
| Glycerin | 18.0 |
| DOPA Liposomes | 5.0 |
| Flavor, Preservatives & Dye | 1.0 |

EXAMPLE 4

Desensitizing Mouthwash (Prophetic) A desensitizing mouthwash in accordance with the invention may be made by mixing the ingredients given below

| Ingredient | Percent by Weight |
| --- | --- |
| Water | 69.0 |
| Potassium Nitrate | 5.0 |
| Alcohol 109 Proof (Grain Alcohol) | 10.0 |
| Glycerin | 10.0 |
| DOPA Liposomes | 1.0 |
| Flavor, Preservatives & Dye | 1.0 |
| Water | q.s. to 100 |

What is claimed is:

1. A dental composition for treating dentinal hypersensitivity comprising a suitable carrier and an effective amount of anionic liposomes, said anionic liposome composition uniquely capable of inducing mineral formation within the dentinal tubules, thereby occluding the tubules, said liposomes having a diameter not greater than the dentinal tubules, in order to penetrate and be retained within said tubules.

2. A dental composition in accordance with claim 1, wherein said liposomes have a diameter not greater than about two microns.

3. A dental composition in accordance with claim 1, wherein said liposomes comprise a potassium salt of diolylphosphatidic acid.

4. A dental composition in accordance with claim 1, wherein said liposomes are present in from about 0.1 to 20 percent by weight.

5. A dental composition in accordance with claim 1, wherein said liposomes additionally provide at least one other agent for the treatment of dentinal hypersensitivity.

6. A dental composition in accordance with claim 5, wherein said other agent is a nerve desensitizing agent.

7. A dental composition in accordance with claim 6, wherein said nerve desensitizing agent is selected from the group consisting of at least one potassium salt, capsaicin, eugenol and mixtures thereof.

8. A dental composition in accordance with claim 7, wherein said at least one potassium salt is selected from the group consisting of potassium bicarbonate, potassium citrate, potassium chloride and potassium nitrate.

9. A dental composition in accordance with claim 6, wherein said composition contains at least one further therapeutic agent useful in oral care formulations in addition to said nerve desensitizing agent.

10. A dental composition in accordance with claim 1, additionally including a source of physiologically acceptable fluoride ion.

11. A dental composition in accordance with claim 10, wherein said source of physiologically acceptable fluoride ion is selected from the group consisting of stannous fluoride, sodium fluoride, potassium fluoride and mixtures thereof.

12. A dental composition in accordance with claim 10, additionally containing a nerve desensitizing agent.

13. A dental composition in accordance with claim 12, wherein said nerve desensitizing agent is selected from the group consisting of at least one potassium salt, capsaicin, eugenol and mixtures thereof.

14. A dental composition in accordance with claim 12, wherein said composition contains at least one further therapeutic agent useful in oral care formulations in addition to said nerve desensitizing agent.

15. A method for reducing dentinal hypersensitivity in a sensitive tooth comprising treating said sensitive tooth with a dental composition comprising a suitable carrier and an effective amount of anionic liposomes, said anionic liposome composition uniquely capable of inducing mineral formation within the dentinal tubules, thereby occluding the tubules, said liposomes having a diameter not greater than the dentinal tubules, in order to penetrate and be retained within said tubules.

16. A method in accordance with claim 15, wherein said liposomes have a diameter not greater than about two microns.

17. A method in accordance with claim 15, wherein said liposomes comprise a potassium salt of diolylphosphatidic acid.

18. A method in accordance with claim 15, wherein said liposomes additionally provide at least one other agent for the treatment of dentinal hypersensitivity.

19. A method in accordance with claim 18, wherein said other agent is a nerve desensitizing agent.

20. A method in accordance with claim 19, wherein said nerve desensitizing agent is selected from the group consisting of at least one potassium salt, capsaicin, eugenol and mixtures thereof.

21. A method in accordance with claim 20, wherein said at least one potassium salt is selected from the group consisting of potassium bicarbonate, potassium citrate, potassium chloride and potassium nitrate.

22. A method in accordance with claim 15, wherein said dental composition additionally includes a source of physiologically acceptable fluoride ion.

23. A method in accordance with claim 22, wherein said source of physiologically acceptable fluoride ion is selected from the group consisting of stannous fluoride, sodium fluoride, potassium fluoride and mixtures thereof.

24. A method in accordance with claim 22, wherein said dental composition additionally contains at least one other agent for the treatment of dentinal hypersensitivity.

25. A method in accordance with claim 24, wherein said other agent is a nerve desensitizing agent.

26. A method in accordance with claim 25, wherein said nerve desensitizing agent is selected from the group consisting of at least one potassium salt, capsaicin, eugenol and mixtures thereof.

27. A method in accordance with claim 25, wherein said composition contains at least one further therapeutic agent useful in oral care formulations in addition to said nerve desensitizing agent.

* * * * *